US00PP16506P3

(12) United States Plant Patent
Hanes

(10) Patent No.: US PP16,506 P3
(45) Date of Patent: May 9, 2006

(54) *VERBENA* PLANT NAMED 'RAP REEDA'

(50) Latin Name: ***Verbena hybrida*×*Verbena tenuisecta***
Varietal Denomination: Rap Reeda

(75) Inventor: Mitchell Eugene Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 292 days.

(21) Appl. No.: 10/846,330

(22) Filed: May 14, 2004

(65) Prior Publication Data

US 2005/0257305 P1 Nov. 17, 2005

(51) Int. Cl.
*A01H 5/00* (2006.01)

(52) U.S. Cl. ..... Plt./308

(58) Field of Classification Search ..... Plt./308
See application file for complete search history.

*Primary Examiner*—Anne Marie Grunberg
(74) *Attorney, Agent, or Firm*—Jondle & Associates P.C.

(57) ABSTRACT

A *Verbena* cultivar particularly distinguished by red colored flowers, dark green foliage and vigorous growth.

1 Drawing Sheet

Genus and species: *Verbena hybrida*×*Verbena tenuisecta*.
Variety denomination: 'Rap Reeda'.

BACKGROUND OF THE NEW PLANT

The present invention comprises a new and distinct cultivar of *verbena*, botanically known as *Verbena hybrida*× *Verbena tenuisecta*, and hereinafter referred to by the cultivar name 'Rap Reeda'. The new cultivar is asexually reproduced from vegetative cuttings and tissue culture resulting from the cross between the female parent 1371-1, a red unpatented proprietary line of *Verbena hybrida*× *Verbena tenuisecta*, and the male parent 1430-3, a rose unpatented proprietary line of *Verbena hybrida*×*Verbena tenuisecta*.

'Rap Reeda' is a product of a planned breeding program intended to create new *verbena* cultivars with red colored flowers, dark green foliage, and vigorous growth.

The new cultivar was created in 2002 in Gilroy, Calif. and has been asexually reproduced repeatedly by vegetative cuttings and tissue culture in Gilroy, Calif.; Andijk, The Netherlands; and Guatemala over a two year period. The plant has also been trialed at Gilroy, Calif.; Litchfield, Mich.; and Andijk, The Netherlands. The present invention has been found to retain its distinctive characteristics through successive propagation, and this novelty is firmly fixed.

DESCRIPTION OF PHOTOGRAPH

This new *Verbena* plant is illustrated by the accompanying photograph which shows blooms, buds, and foliage of the plant in full color, the colors shown being as true as can be reasonably obtained by conventional photographic procedures.

The photograph shows the mature plant with an inset photo of a close-up of the inflorescence.

DESCRIPTION OF THE NEW CULTIVAR

The following detailed descriptions set forth the distinctive characteristics of 'Rap Reeda'. The data, which define these characteristics, were collected from asexual reproductions carried out in Gilroy, Calif. The plant history was taken on 7 month old plants grown in one-gallon pots in the Fall/Winter season, in a double poly-greenhouse under natural light and color readings were taken in the greenhouse under natural lights. Color references are primarily to The R.H.S. Colour Chart of The Royal Horticultural Society of London (R.H.S.) 2001. Texture description details were observed under a dissecting microscope according to The New Royal Horticultural Society Dictionary of Gardening (1992).

THE PLANT

Classification: *Verbena hybrida*×*Verbena tenuisecta*.
Botanical: *Verbena*.
Commercial: 'Rap Reeda'.
Form: Low trailing annual, decumbent.
Growth and branching habit: Vigorous growing, moderate basal branching, trailing habit.
Height: From soil level to top of blooms: Approximately 8–10 cm.
Width: Approximately 40–50 cm.
Time to produce a finished flowering plant: 11 weeks.
Outdoor plant performance: Typical bedding plant culture, full sun; used as a hanging plant, in a mixed container planting or mass planting in a bed.
Time to initiate and develop roots: Approximately 4–10 days in the greenhouse.
Root description: Fibrous, fleshy, white.

THE LEAVES

Leaf length: 3.5–4.5 cm.
Leaf width: 2.0–2.5 cm.
Leaf blade shape: Ovate.

Leaf margin: Pinnatisect/incised.
Apex aspect: Acute.
Base aspect: Acuminate.
Leaf color: Upper side — RHS 137A (green) and 138A (green); Underside RHS 138A (green).
Foliage texture: Hirsute.
Venation: Palmate.
Venation color: RHS 144B (yellow-green).
Petiole length: 0.4–0.5 cm.
Petiole diameter: 0.1 cm.
Petiole color: RHS 144B (yellow-green).
Petiole texture: Hirsute.

THE STEM

Length: 20–30 cm.
Diameter: 0.2 cm.
Stem internode length: 1.5–2.0 cm.
Color: RHS 144A (yellow-green).
Texture: Hirsute.
Stem anthocyanin: None.

THE BUD

Shape: Linear.
Diameter: 0.1–0.15 cm.
Length: 1.5 cm.
Color at tight bud: RHS 182A (red).

THE FLOWER

Blooming habit: Flowers continuously throughout the growing season.
Inflorescence type: Spike.
Spike diameter: 3.0–3.5 cm.
Spike depth: 3.0–3.5 cm.
Peduncle length: 3.0–3.5 cm.
Peduncle diameter: 0.1–0.15 cm.
Peduncle color: RHS 144A (yellow-green).
Peduncle texture: Hirsute with glandular hairs.
Flower color: Front side, RHS 46B (red) but darker; RHS 155A (white) but whiter, small "eye" spot.
Flower color: Underside, RHS 43B (red).
Floret form: Salverform; sessile on spikes.
Floret (limb) diameter: 1.0–1.5 cm.
Corolla tube length: 1.1–1.3 cm.
Number of florets per spike: 30–40.
Number of petals: Gamopetalous, five lobed.
Petal size: Length of one lobe — 0.6–0.7 cm; width of one lobe — 0.5–0.6 cm.
Petal lobe shape: Obcordate.
Petal apex shape: Emarginate.
Petal base shape: Fused.
Petal margin: Entire.
Petal texture: Papillose.
Sepals: Five sepals whose margins are fused to each other along their length with a transparent membrane of less than 1 mm in width with one smaller sepal (7 mm) attached to the base of the calyx.
Calyx length: 0.9–1.0 cm.
Calyx width: 0.1 cm.
Calyx shape: Linear.
Calyx apex: Acute.
Calyx color: Between RHS 146B and C (green).
Longevity of individual blooms: 5–7 days.
Fragrance: None.

THE REPRODUCTIVE ORGANS

Stamens: Anthers and filaments fused to upper half of corolla tube; four anthers with two pollen sacs per anther.
Pollen amount: Moderate.
Pollen color: RHS 11D (Yellow).
Pistil: One style approximately 1.3 cm.
Fruit seed set: Does not freely set seed but can produce 4 narrow nutlets, approximately 4 mm long and enclosed in the dried calyx.

DISEASE AND INSECT RESISTANCE

Mildew tolerance.

COMPARISON WITH KNOWN CULTIVARS

'Rap Reeda' has slightly smaller flowers than the female parent, 1371-1. 'Rap Reeda' also has an eye spot whereas the female parent does not have an eye spot. Additionally, the female parent is more sensitive to powdery mildew than 'Rap Reeda'.

'Rap Reeda' has a brighter red colored flower than the rose colored male parent, 1430-3. 'Rap Reeda' also has an eye spot whereas the male parent does not have an eye spot. 1430-3 is a more compact plant than 'Rap Reeda'.

I claim:

1. A new and distinct cultivar of *Verbena* plant as shown and described herein.

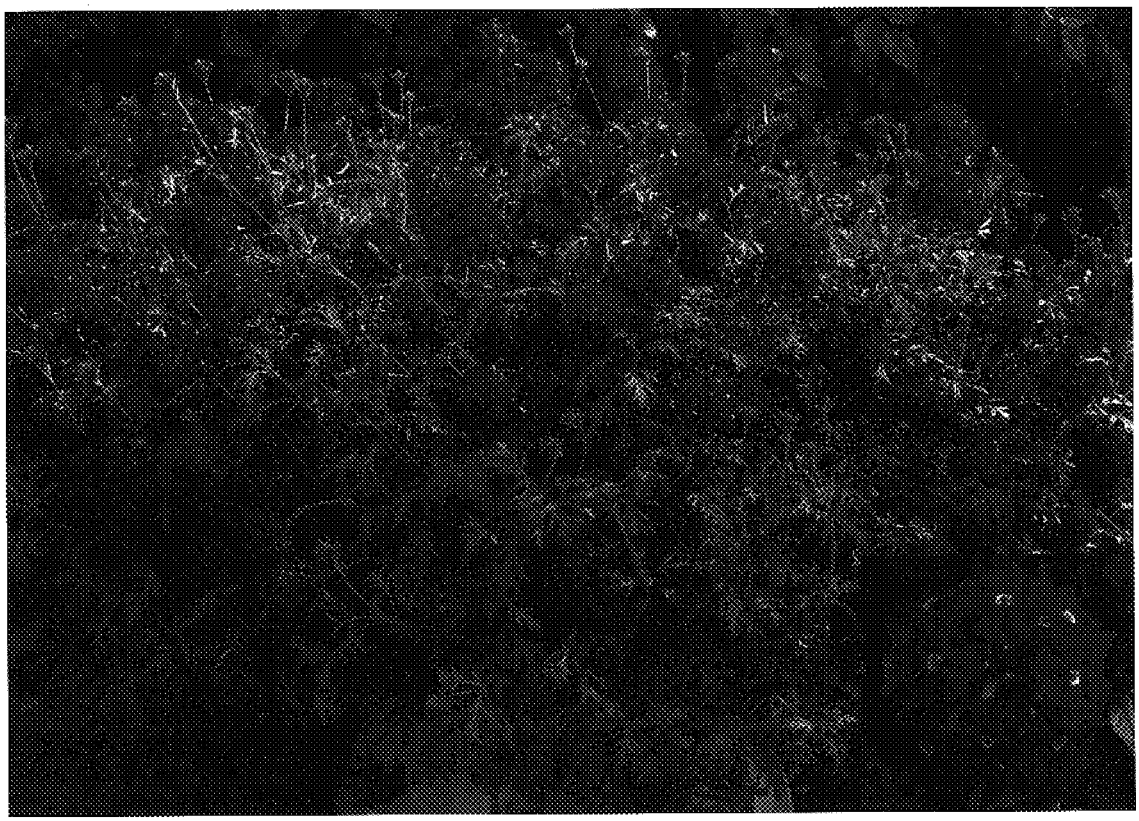

* * * * *